(12) United States Patent
Clifford et al.

(10) Patent No.: US 9,308,094 B2
(45) Date of Patent: Apr. 12, 2016

(54) ACTIVE AND PASSIVE DEVICES FOR REDISTRIBUTING FORCES FOR THE MEDIAL AND LATERAL KNEE

(71) Applicant: Moximed, Inc., Hayward, CA (US)

(72) Inventors: Anton G. Clifford, Mountain View, CA (US); Andrew H. Jones, San Jose, CA (US)

(73) Assignee: MOXIMED, INC., Hayward, CA (US)

( * ) Notice: Subject to any disclaimer, the term of this patent is extended or adjusted under 35 U.S.C. 154(b) by 32 days.

(21) Appl. No.: 13/894,267

(22) Filed: May 14, 2013

(65) Prior Publication Data

US 2013/0304208 A1 Nov. 14, 2013

Related U.S. Application Data

(60) Provisional application No. 61/464,738, filed on May 14, 2012, provisional application No. 61/784,774, filed on Mar. 14, 2013.

(51) Int. Cl.
| | | |
|---|---|---|
| *A61F 2/38* | (2006.01) | |
| *A61F 2/30* | (2006.01) | |
| *A61B 17/80* | (2006.01) | |
| *A61B 17/56* | (2006.01) | |

(52) U.S. Cl.
CPC . *A61F 2/38* (2013.01); *A61B 17/56* (2013.01); *A61B 17/8061* (2013.01); *A61B 2017/564* (2013.01); *A61B 2017/567* (2013.01)

(58) Field of Classification Search
USPC .......... 623/17.11–17.13, 18.11, 20.14–20.28
See application file for complete search history.

(56) References Cited

U.S. PATENT DOCUMENTS

| | | | |
|---|---|---|---|
| 5,171,276 A | 12/1992 | Caspari et al. | |
| 6,629,997 B2 | 10/2003 | Mansmann | |
| 2008/0275567 A1* | 11/2008 | Makower et al. | 623/23.41 |
| 2010/0114322 A1 | 5/2010 | Clifford et al. | |
| 2011/0213466 A1 | 9/2011 | Shenoy et al. | |
| 2011/0282255 A1* | 11/2011 | Nace | 602/16 |
| 2013/0304208 A1 | 11/2013 | Clifford et al. | |

FOREIGN PATENT DOCUMENTS

KR 10-2012-0068827 A 6/2012

OTHER PUBLICATIONS

International Search Report and Written Opinion for PCT Patent App. No. PCT/US2014/024195 (Aug. 12, 2014).

\* cited by examiner

*Primary Examiner* — Yashita Sharma
(74) *Attorney, Agent, or Firm* — Adam J. Cermak; Cermak Nakajima & McGowan LLP

(57) ABSTRACT

Implant apparatus and methods directed toward treating conditions involving the knee joint are disclosed. Full range of motion of the knee joint and tissue integrity are maintained in treatment approaches. In one particular approach, osteoarthritis of the knee joint is addressed by unloading one or more of the lateral and medial compartments.

7 Claims, 13 Drawing Sheets

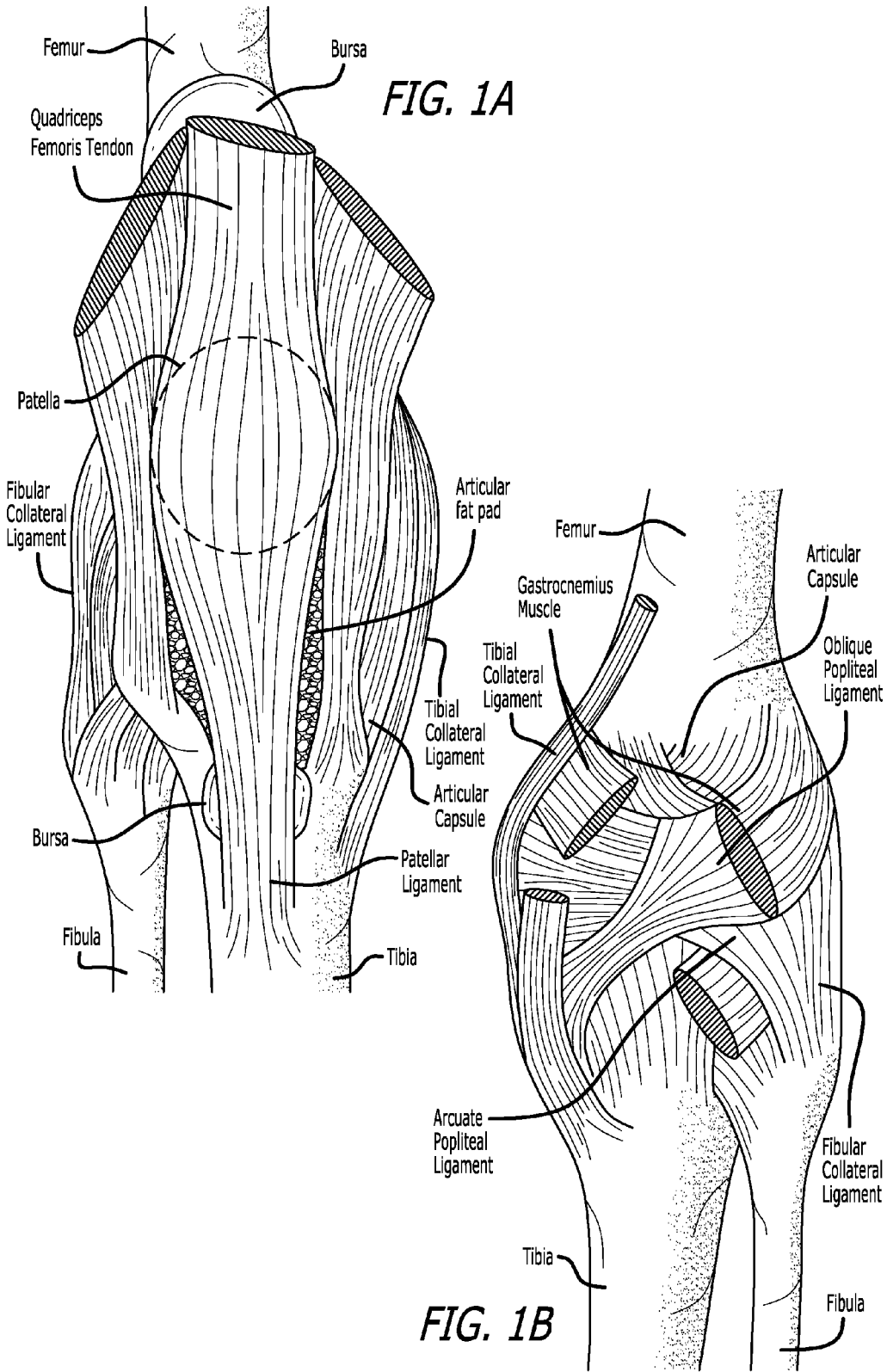

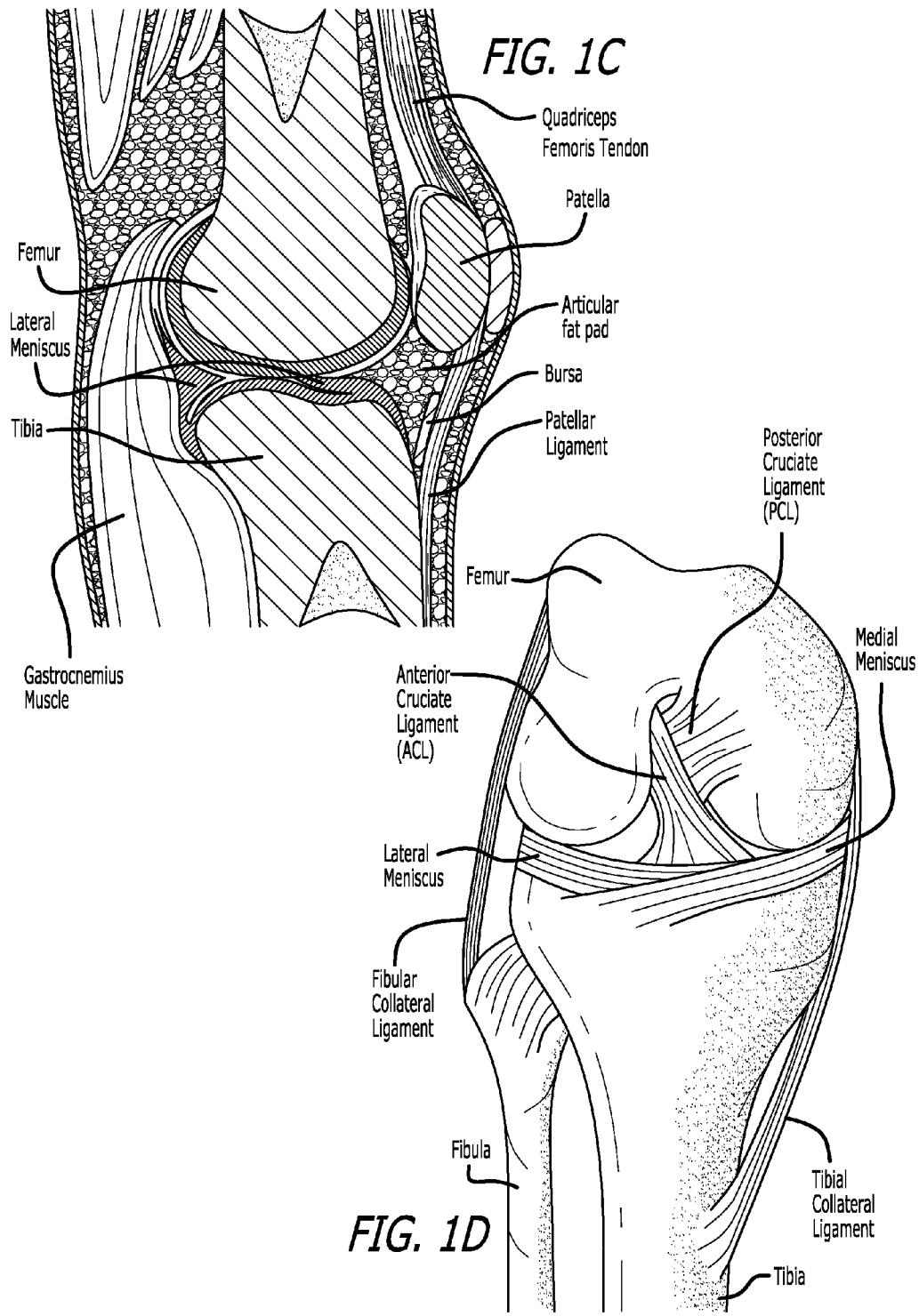

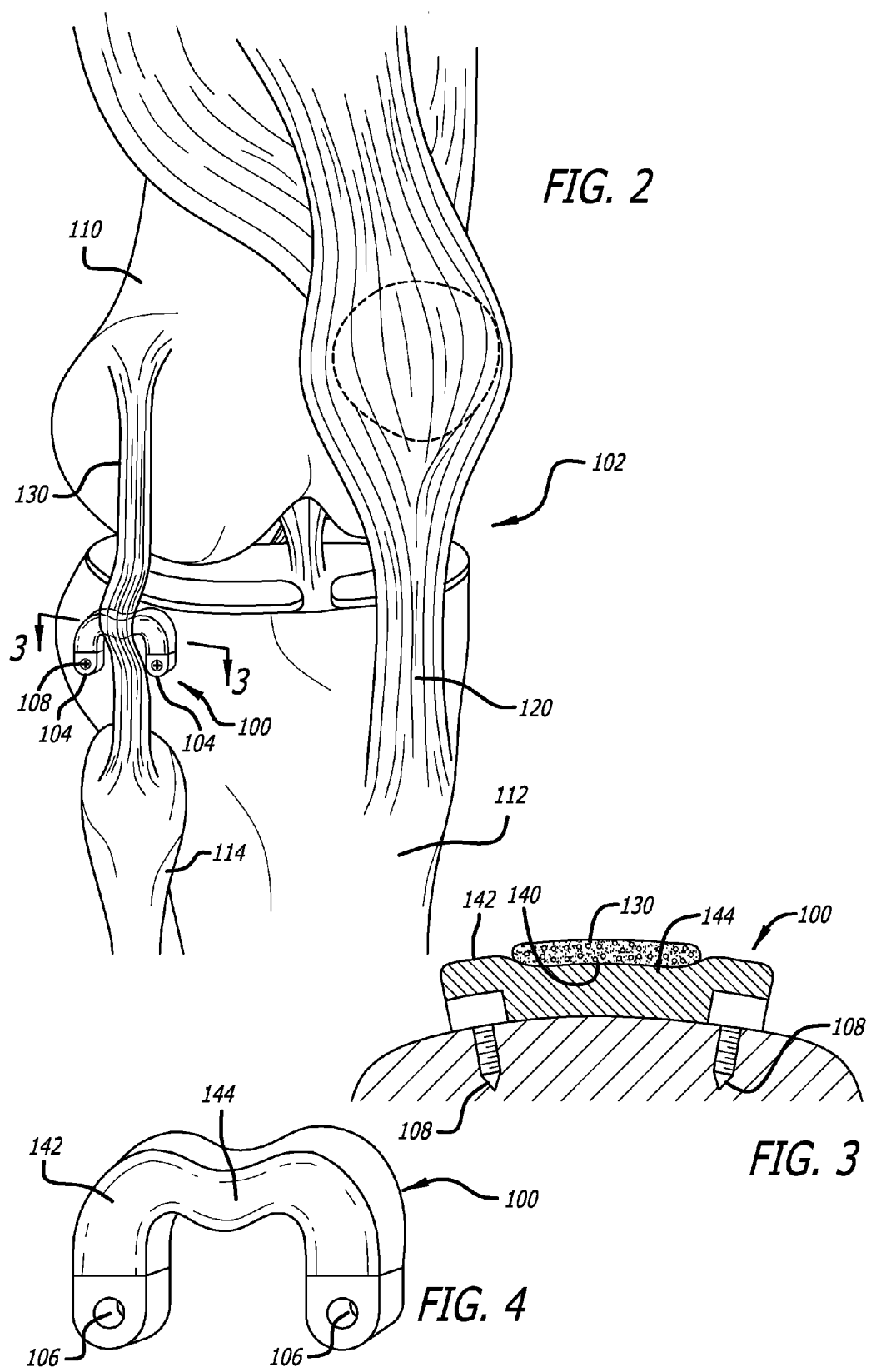

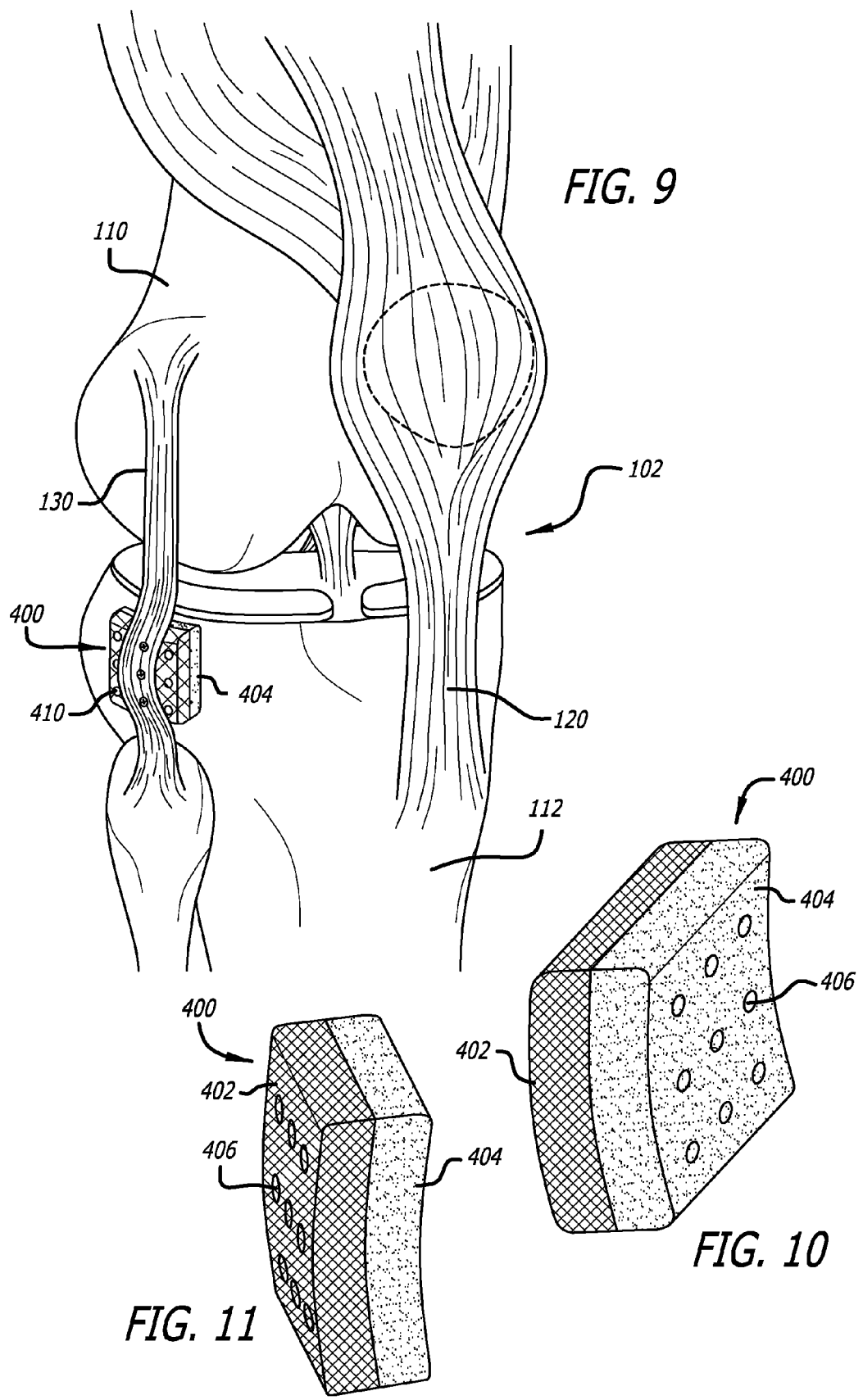

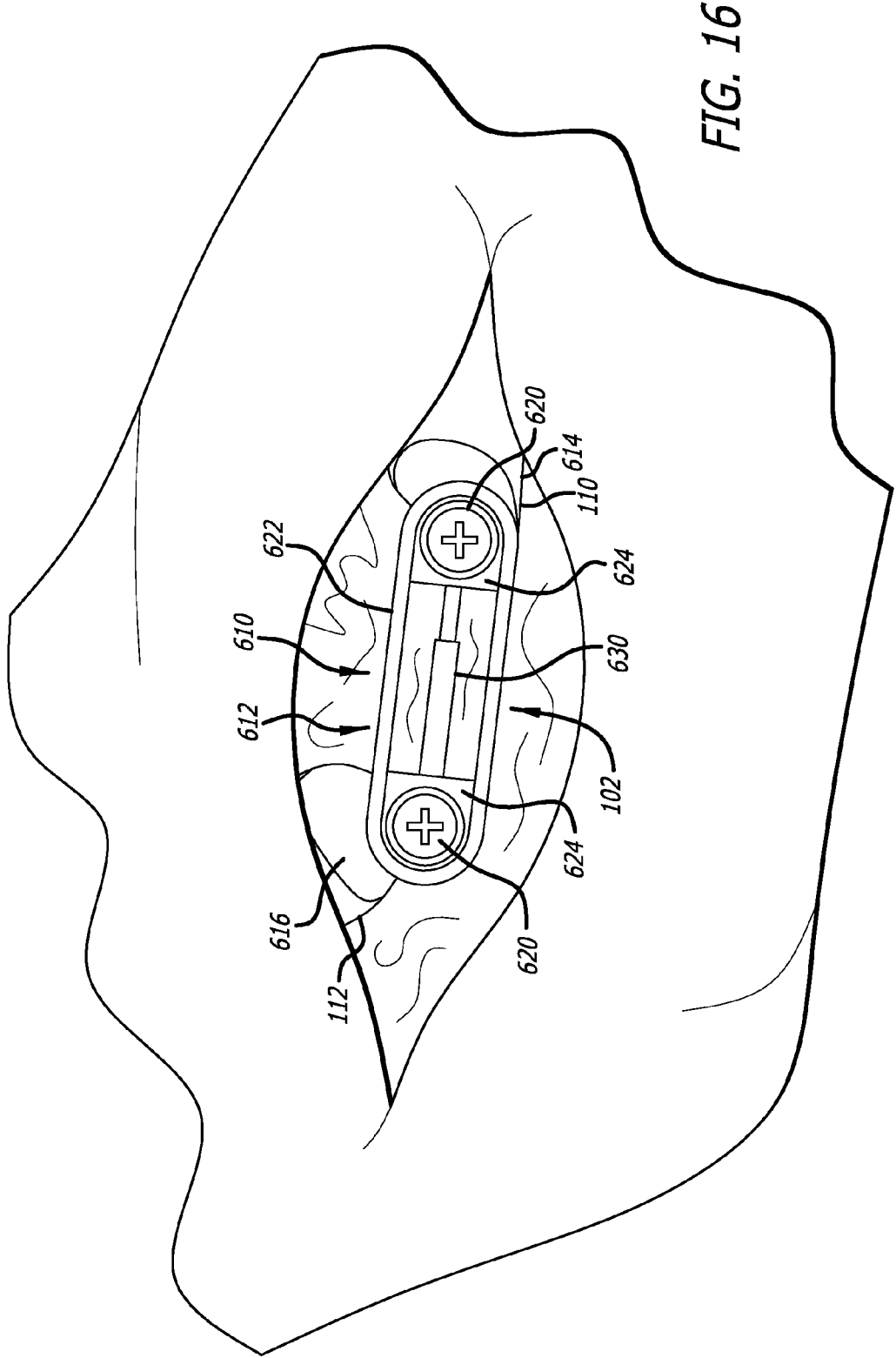

ACTIVE AND PASSIVE DEVICES FOR REDISTRIBUTING FORCES FOR THE MEDIAL AND LATERAL KNEE

CROSS REFERENCES TO RELATED APPLICATIONS

This application claims the benefit of U.S. Application Ser. No. 61/646,738, filed May 14, 2012, and U.S. Application Ser. No. 61/784,774, filed Mar. 14, 2013, the entire disclosures of which are expressly incorporated herein.

BACKGROUND

The present disclosure is directed towards systems and methods for treating tissue of a body and more particularly, towards approaches designed to treat a natural joint and conditions involving the knee joint specifically.

A joint is the location at which two or more bones make contact. They are constructed to allow movement and provide mechanical support, and are classified structurally and functionally. Structural classification is determined by how the bones are connected to each other, while functional classification is determined by the degree of movement between the articulating bones. In practice, there is significant overlap between the two types of classifications.

There are three structural classifications of joints, namely fibrous or immovable joints, cartilaginous joints and synovial joints. Fibrous/Immovable bones are connected by dense connective tissue, consisting mainly of collagen. The fibrous joints are further divided into three types: sutures which are found between bones of the skull; syndesmosis which are found between long bones of the body; and gomphosis which is a joint between the root of a tooth and the sockets in the maxilla or mandible.

Cartilaginous bones are connected entirely by cartilage (also known as "synchondroses"). Cartilaginous joints allow more movement between bones than a fibrous joint but less than the highly mobile synovial joint. Synovial joints have a space between the articulating bones for synovial fluid. This classification contains joints that are the most mobile of the three, and includes the knee and shoulder. These are further classified into ball and socket joints, condyloid joints, saddle joints, hinge joints, pivot joints, and gliding joints.

Joints can also be classified functionally, by the degree of mobility they allow. Synarthrosis joints permit little or no mobility. They can be categorized by how the two bones are joined together. That is, synchrondoses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Finally, diarthrosis joints permit a variety of movements (e.g. flexion, adduction, pronation). Only synovial joints are diarthrodial and they can be divided into six classes: 1. ball and socket—such as the shoulder or the hip and femur; 2. Hinge—such as the elbow; 3. Pivot—such as the radius and ulna; 4. condyloidal (or ellipsoidal)—such as the wrist between radius and carps, or knee; 5. Saddle—such as the joint between carpal thumbs and metacarpals; and 6. Gliding—such as between the carpals.

Synovial joints (or diarthroses, or diarthroidal joints) are the most common and most moveable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibro-cartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Maladies that can affect the knee joint specifically can be due to misalignment or dislocation. Pain can exist when there is an excess of force contact between the tibia and femur. This can be due to misalignment associated arthritis or anatomical conditions specific to an individual. These problems usually occur toward the medial or lateral sides of the leg and during portions of the gait cycle.

Various muscles and ligaments run along the human leg and certain of these extend across a knee joint (See FIGS. 1A-D). On the lateral side of the knee, a lateral (fibular) collateral ligament extends from the femur to the fibula and an iliotibial band extends from the upper leg to the tibia. The tendon of popliteus also runs between the femur and lower leg and includes a length along the lateral side of the knee as well as a portion which wraps about the back of the knee and connects to the popliteus muscle. The medical (tibial) collateral ligament extends across the knee on a medial side of the joint, as does the arcuate ligament. In the front of the knee, there is the quadriceps tendon above and connected to the kneecap and below and extending from the kneecap is the patellar ligament. Within the knee, there are the anterior cruciate ligament and posterior cruciate ligament. Further, the knee anatomy includes the articular capsule which contains the patella, ligaments, menisci and bursai. Each of such structures can be misaligned or affected by disease causing unnatural gait or individual specific problems.

The knee joint is capable of flexion and extension motions and can undergo slight rotational movement. It is this rotational component that accounts for the frequency of knee injuries. In fact, tissue injury can manifest as swelling about the knee, inability to bear weight or loss of function. Fractures that enter the knee joint often render the joint defective and the once smooth joint surface made irregular. Additionally, fractures resulting in improper limb alignment may contribute to long-term morbidity like arthritis, instability, and functional loss of motion.

The stabilizing ligaments of the knee include the medial collateral ligament (MCL) and lateral collateral ligament (LCL), and are located outside the knee joint proper. The anterior cruciate ligament (ACL) and posterior cruciate ligament (PCL) are stabilizer ligaments located within the knee joint. The patellar ligament is located outside the knee joint and functions to provide support for the knee by shielding it, and strengthening the actions of the quadriceps femoris muscle. In particular, the collateral ligaments resist widening of the knee joint. The cruciate ligaments, which are within the knee joint proper resist hyperflexion and hyper extension and also slight rotational movements of the knee. Articular cartilage is bathed by synovial fluid that lubricates the knee joint.

When these ligaments cannot function as intended due to trauma, injury or disease such as arthritis, an individual's knee will not operate properly and pain can result. Conventional treatments have included major surgery where diseased areas of bone are removed or re-shaped or when ligaments are moved or reattached. Such approaches are of course highly invasive and can involve extended periods of recovery and can have limited success.

It has additionally been observed that joints can suffer from specific patterns of disease. For example, lateral osteoarthritis of a joint such as the knee is characterized by a disease pattern tending to be a flexion based disease. As discussed above, the lateral knee has a more complex anatomy than the medial knee and has associated therewith a number of unique neighboring musculoskeletal, vascular and neurological structures, which thereby limit implant real estate. The motion of the lateral knee is also much broader than the medial knee. Such particular patterns of disease can thus necessitate highly specific treatment approaches.

Recently, various approaches to force redistribution in a knee joint have been proposed. In fact, it has been contemplated to insert implants below the patellar tendon, lateral quadriceps-patellar tendon, the biceps femoris tendon, iliotibial band, lateral gastrocnemius, popliteus or fibular collateral ligament to accomplish lateral displacement to realign force vectors and other moment arms loading the knee joint.

Sufficient attention does not appear to have been given in prior joint force redistribution approaches, however, to treatment of the knee joint throughout its full range of motion. Lateral osteoarthritis treatment approaches including those which operate specifically in a manner which unloads a joint in flexion also appear to be lacking. There is a further perceived need for avoiding negative remodeling of the knee ligaments as well as approaches to maintain a desired alignment of an implant and target tissue.

Therefore, what is needed and heretofore lacking in prior attempts to treat joint pain associated with misalignment or dislocation is an implantation method and implant device which addresses full range of joint movement, and which maintains desired structural integrity of anatomy forming the knee joint. There is thus also a need for both passive and active devices for accomplishing desired joint treatments.

The present disclosure addresses these and other needs.

SUMMARY

Briefly and in general terms, the present disclosure is directed towards treating joint structures. In one aspect, there are disclosed approaches to redistributing forces of the joint to alleviate pain or to address misalignment.

In one particular embodiment, there is provided an implant which is contoured to receive a tendon of the knee. The contour of the implant is configured to define structure preventing the tendon from disengaging from the implant during a full range of motion of a knee joint. The implant is also contoured to avoid negative remodeling of the tissue of the knee.

The implant can embody a fluid filled bladder which self-contours to tissues. In one aspect, the implant can be adjustable through the movement, addition or removal of fluid. Various embodiments are contemplated to treat knee joint misalignment and to inhibit dislocation, as well as to absorb unnatural loads applied by the bones of the joint upon adjacent anatomy.

In a specific approach, an implant can include a two stage bladder having a main chamber for positioning under a ligament and a secondary chamber in communication with the main chamber. A valve can further be provided between the main and secondary chambers. During gait, fluid remains in the main chamber and performs ligament tensioning. During rest periods and when the limb is straight, fluid passes to the secondary chamber relieving tension on the ligament. This prevents negative remodeling or stretching of the ligament, as the same causes such therapy to become less effective over time.

An implant can include a chamber that is fluid or gas filled to provide a compliant bolster and lengthening effect to increase a moment arm of the bolstered tendon or muscle. The chamber and bladder can be inflated or expanded over time to provide an increasing size or stiffness structure, or deflated or contracted to provide an opposite effect. A valve or injection port can be utilized for this functionality.

The implant can further be configured such that when a leg is in extension, there is no force or little force in a first chamber of the implant. An elasticity of a second chamber is selected to cause fluid to flow into the first chamber. During gait, a valve between the chambers retains fluid within the first chamber. When at rest, with the joint in flexion the tendon presses fluid from the first chamber into the second chamber.

In yet another approach, an implant is provided to treat a joint and functions to redistribute forces of a knee joint. The implant includes structure accomplishing attachment of the implant to the target tendon. This implant can be a single spacer or can include one or more chambers that contain fluid or gas. Such an implant thus remains in place during a full range of motion of a knee joint.

An approach specific to treating lateral osteoarthritis of a joint is also disclosed. An active unloading device assembly can be employed to unload a lateral knee compartment by implanting the assembly on a medial side of the joint. In one specific approach, the assembly is configured to impart varizing load to the joint and to unload the lateral compartment. The assembly can include an extendable tension loop which applies the desired varizing force. In one embodiment, the active unloading assembly includes a first base configured to be affixed to a first bone of a joint and a second base configured to be affixed to a second bone of a joint. Extending from each base can be a projection about which a collar can be coupled in an articulating arrangement. A piston can be further provided between the collars. The extendable tension loop is configured about the collars and across a joint to provide the desired varizing load.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIGS. 1A-D are various views, depicting the anatomy of a knee joint;

FIG. 2 is a perspective view, depicting an implant attached to members defining a joint;

FIG. 3 is a cross-sectional view, depicting the structure of FIG. 2 taken along line 3-3;

FIG. 4 is a perspective view, depicting the implant of FIG. 2;

FIG. 9 is a perspective view, depicting another embodiment of an implant;

FIGS. 10 and 11 are perspective views, depicting the implant of FIG. 9;

FIG. 16 is a top view, depicting one approach to an active unloading assembly;

DETAILED DESCRIPTION OF THE PREFERRED EMBODIMENTS

Figure 4A:
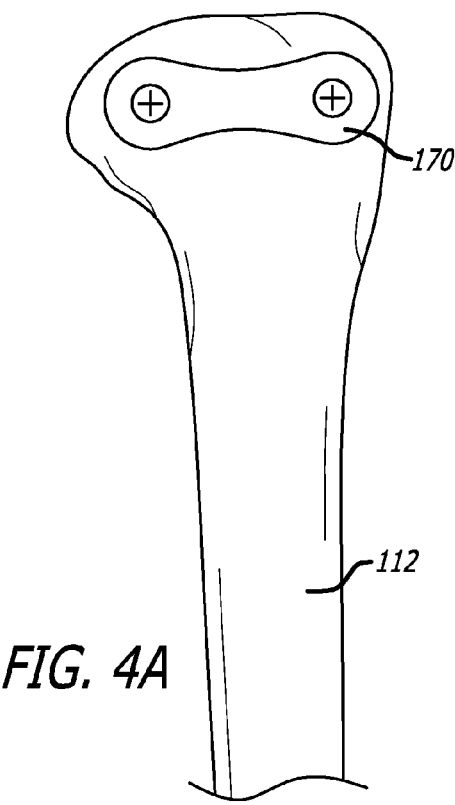
FIGS. 4A and 4B are perspective views of alternative shaped implants attached to a member of a joint.

Referring now to the drawings, which are provided by way of example and not limitation, the present disclosure is directed towards apparatus and methods for treating the knee joint. Misalignment or dislocation can be due to natural anatomy specific to an individual or can be a function of a disease or condition, such as arthritis. Significant pain can be associated with these conditions and can be a direct result of excessive forces being generated between joint members. In particular, pain results when there are undesirable force contacts between the tibia and the femur or through inadequate anatomy separating these bones. The present disclosure is directed at both passive and active devices for alleviating pain by redirecting or absorbing excess forces without permanently remodeling tissues critical to the functioning of the knee joint.

As shown in FIG. 1-4, one approach to treating conditions involving a knee can include the placement of a spacer or an implant 100 at the knee joint 102. The implant 100 can be generally U-shaped and can include terminal ends 104 configured to be affixed to body anatomy. In one approach, the terminal ends 104 include through holes 106 sized and shaped to receive bone screws 108 or other affixation structure. In this way, the implant 100 can be attached directly to a femur 110, tibia 112 or fibula 114 of the knee joint 102. Although the implants have been described herein as attached to a bone surface beneath a tendon, the implants can also reside beneath other anatomical structures including ligaments and muscles or a combination of anatomical structures. The implant can function to apply a tensioning force to all of the surrounding structures in combination (i.e. displacing both tendon and muscle tissue) to adjust alignment of the joint and redirect forces transmitted through the joint.

As shown in FIG. 1, the implant 100 is affixed to the tibia 112 such that a midsection 120 of the implant 100 is configured under a ligament or tendon 130. Here, the implant is shown positioned under the fibular collateral ligament, but it is to be appreciated that the implant can be arranged under any knee structure so long as the desired redistribution of forces is accomplished. The terminal ends 104 of the implant 100 are shown directed away from the knee joint 102 but can alternatively be pointing toward the knee joint 102.

The implant 100 is further contoured to define a anatomically matching structure. It is thus contemplated that a lower surface 140 of the implant 100 be curved to mimic the shape of the structure to which the implant engages, such as the tibia 112 or femur 110. An upper surface 142 is also contoured so as to fit nicely with the knee anatomy and may include a lubricious coating or material permitting relative motion between the implant and knee anatomy.

In one embodiment, the upper surface 142 further includes a recess 144 designed to receive the tendon 130. The recess 144 defines a trough through which the tendon 130 can be translated throughout a full range of articulation and valgus and varus motion or other rotation or movement of the knee joint. Thus, a portion of the tendon 130 remains within the recess 144 throughout gait as well as when the knee joint is in complete flexion or extension, and all angles therebetween, and when the knee joint is loaded and unloaded. The trough 144 may be used to prevent the tendon from slipping off of the implant in the anterior or posterior directions. However for a wider or more stable ligament or tendon, no recess or trough may be needed.

The implant 100 can be configured to include one or more structure that only applies tension during gait, and then, during only portions of the gait cycle. Such structure can also include a load absorption component acting during such intervals. Through this approach, undesirable permanent remodeling of knee structure, and in particular unwanted lengthening of the tendon can be avoided.

Figure 4B:
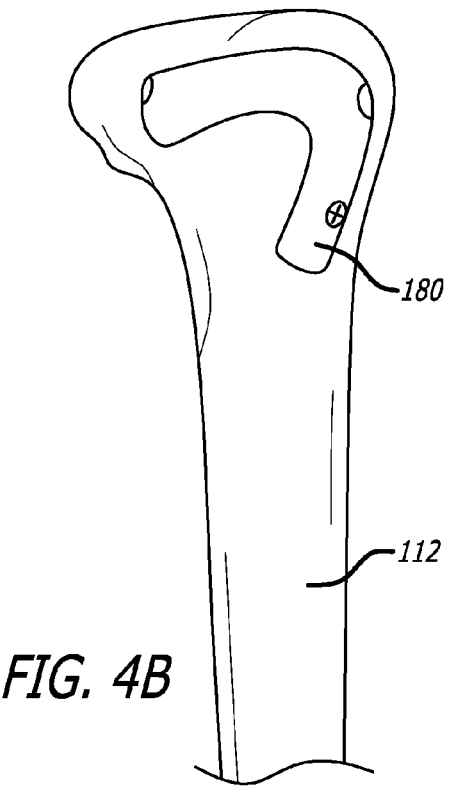

Although a U-shaped implant is shown, other shapes may also be used as long as the implant includes sufficient area for securing the implant to the bone. Examples of other implant shapes include I-shaped, L-shaped or H-shaped. FIGS. 4A and 4B illustrate an implant 170 having an I-shape and an implant 180 having an L-shape.

Figure 5:
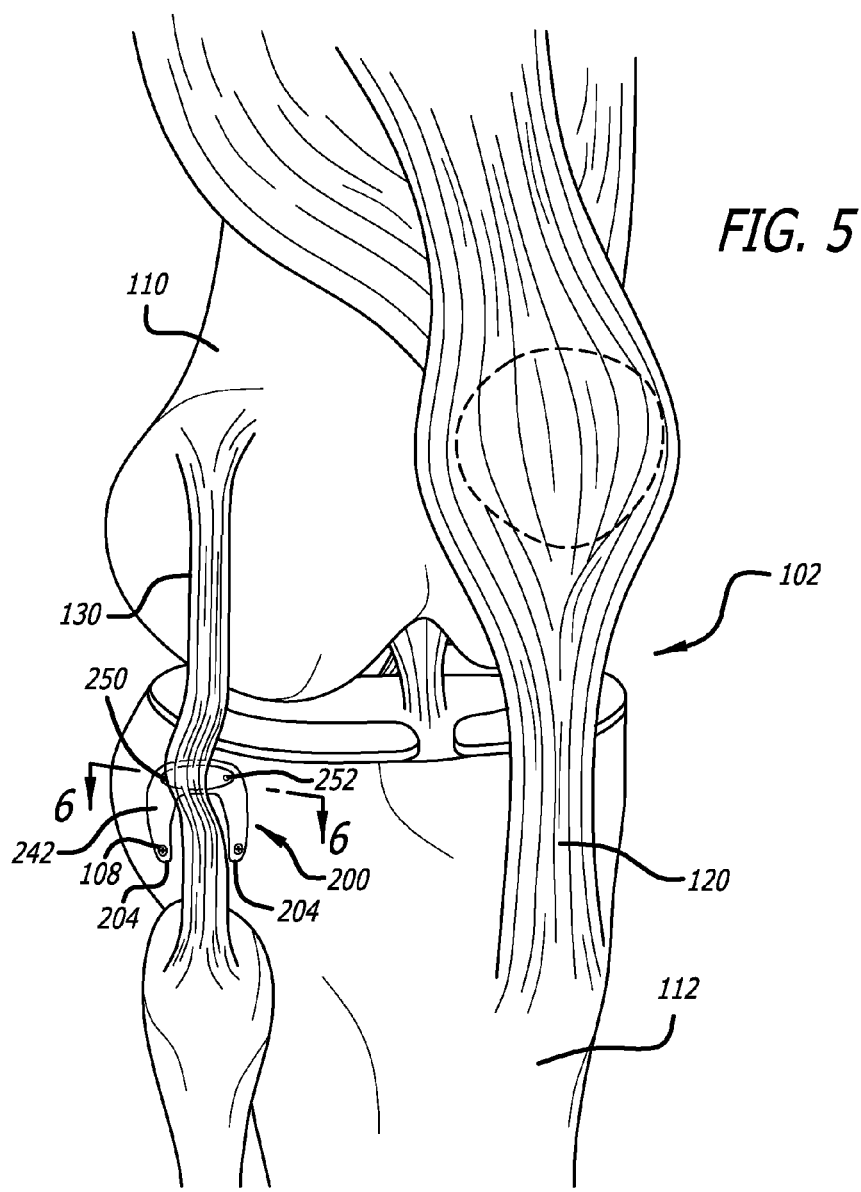
FIG. 5 is a perspective view, depicting another embodiment of an implant attached to members defining a joint.
Figure 6:
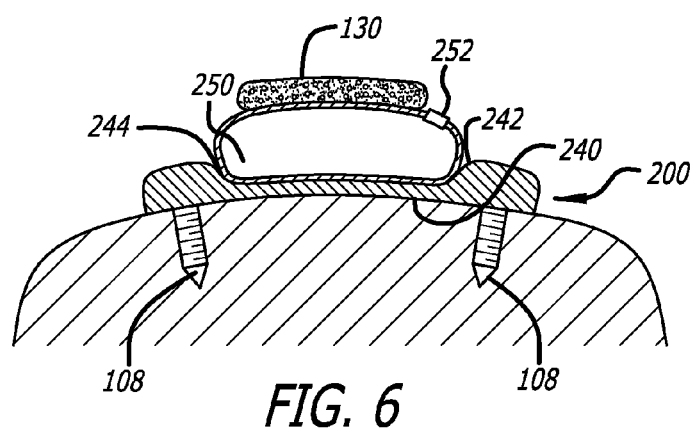
FIG. 6 is a cross-sectional view, depicting the structure of FIG. 5 taken along lines 6-6.

Referring to FIGS. 5 and 6, there is shown another embodiment of a spacer or an implant 200. As before, the implant can be generally U-shaped and includes terminal ends 204 configured to be affixed to body anatomy. Again, through holes 206 are provided to receive affixation structure such as bone screws 108 so that the implant can be attached directly to knee anatomy. An upper surface 242 of the implant 200 is intended to be lubricous to permit relative movement with a tendon 130. Moreover, the implant can be configured with its terminal ends 204 directed toward or away from the knee joint 102 and can include a midsection 220 with a recess 244 shaped to receive the tendon 130 through a full range of motion of the knee.

This embodiment of the implant further includes a fluid, gas or gel filled chamber or bladder 250 which is accessible by an injection port 252. The chamber 250 can form an integral structure with remaining portions of the implant 200 and portions of the implant 200 can embody fiber woven reinforced fixation material to form a single bodied structure. The injection port 252 is employed to both place substances within the chamber 200 and to be accessible to alter the volume or composition of the substance before and after implantation. The port can also be used to remove all or most fluid when implanting or removing the device or to alter the softness or rigidity of the implant. The structure defining the chamber 250 can have an elasticity greater than that chosen for the remaining portions of the implant 200, such as for example the terminal ends 204 which are designed to have a rigidity or robustness suited for permanent attachment to knee anatomy. The materials are of course chosen to be biocompatible in any event.

The substance chosen to fill the chamber 250 is selected to cooperate with the material chosen for walls defining the chamber 250 so that desired tensioning and load absorption can be effectuated. It is further contemplated to take advantage of fluid responses of the substances chosen for placement within the chamber 250. For example, a viscous fluid or gel such as silicone hydrogel flows smoothly under low strain rates, but resists flow under high strain rates. Therefore, the fluid or gas chosen is intended to have a viscosity and the chamber walls are designed to have a flexibility to transmit tension along the tendons and to absorb excess forces so as to alleviate pain. Such tension and load manipulation can be reserved to occur only during gait, and for that matter, during only portions of gait. During rest, or otherwise when there is no pain due to forces associated with the this manipulation is removed so that undesirable remodeling is avoided.

Thus, as the knee joint articulates during gait, the tendon 130 is guided through the implant recess 244. The tension transferring and load absorbing chamber 250 is sized and shaped to span the recess 244 so that during certain portions of gait, tension is transferred along the tendon 130 and forces generated through the tendon 130 are absorbed in a manner to relieve pain associated with the unnatural engagement of knee anatomy. For example, forces between the tibia 104 and the femur 102 can be alleviated and angles with which these bones are moved relative to adjacent anatomy can be altered to thereby minimize pain.

Figure 7:
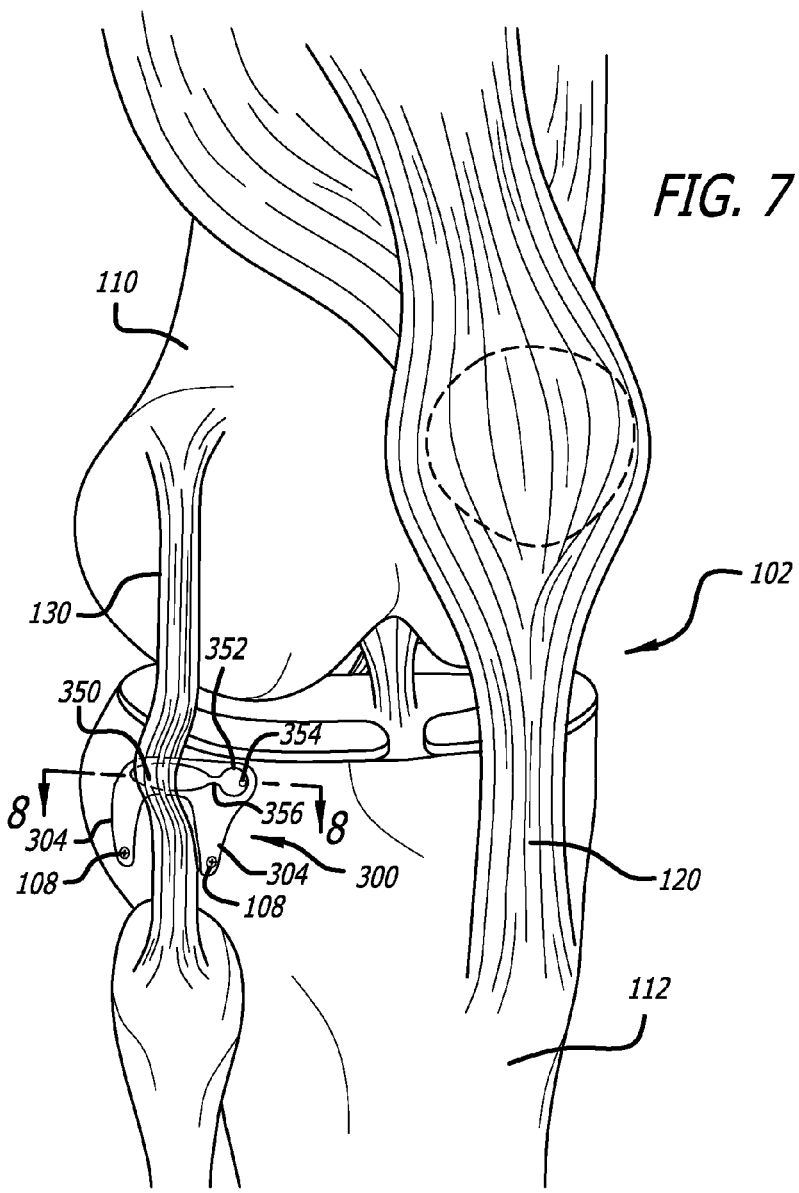
FIG. 7 is yet another perspective view, depicting another embodiment of an implant attached to members defining a joint.
Figure 8:
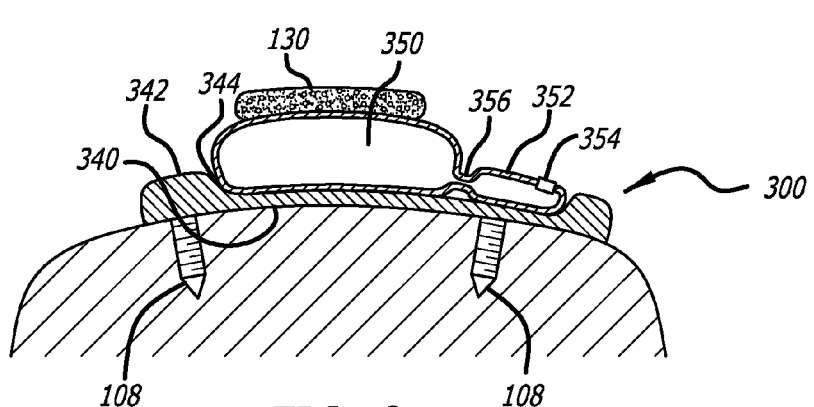
FIG. 8 is a cross-sectional view, depicting the structure of FIG. 7 taken along lines 8-8.

In yet another approach (FIGS. 7 and 8), the implant 300 can further include multiple chambers 350, 352 that are in fluid communication and which are versatile in accommodating tension and contact forces. The generally U-shaped device can be extended to provide a platform about each of the chambers 350, 352. Here, again, the chambers 350, 352 are designed to receive gases or fluids which embody desirable viscosity characteristics. Additionally, the first chamber 350 is intended to be arranged to be in apposition with the tendon 130 and the second chamber 352 is to be positioned remote from the tendon 130. Also, as before, the walls defining the chambers 350, 352 are formed from materials having an elasticity designed to achieve desired tension and contact force manipulation throughout the full range of motion of the knee joint. An injection port 354 is additionally included to provide access to the second chamber 352 so that the volume or composition of the substance in the chamber can be altered.

A neck 356 joining the first 350 and second 352 chambers provides the fluid communication between the structures. A valve (not shown) can be configured in this area or the neck can define a small opening. In either approach, the neck 356 can be configured to play a role in the movement of fluid from one chamber to the next. For example, when a leg of an individual is in extension, there is no force or little force on the first chamber 350. The elasticity of the second chamber 352 is chosen to thus cause fluid to flow into the first chamber 350. During gait, the sizing of the neck 356 is such that its flow access is limited so that there is insufficient time for fluid to pass from the first chamber 350 to the second chamber 352. Rather, the fluid remains but flows within the first chamber 350 to thereby provide tension and contact force manipulation and absorption. When seated or otherwise placing the knee joint in other resting or non-gait positions, with the joint in flexion, the force of the tendon 130 presses fluid out of the first chamber 350 into the second chamber 352. As such, the first chamber 350 is reduced in size during this juncture, and the tendon is not subjected to tension and force manipulation. By not engaging in this manipulation, the tendon 130 can be unloaded and remodeling thereof is avoided.

In a related approach, as shown in FIGS. 9-11, an implant 400 designed to accomplish tension and contact forces manipulation can be affixed directly to the tendon 130. This implant 400 can further include one or more of the features described above including one or more fluid filled chambers. Further, it is again contemplated that the device be formed from biocompatible materials. This particular implant 400 further embodies a porous or mesh tendon contacting surface 402 and a lubricious bearing surface 404. The porous mesh surface 402 supports ligament ingrowth and aids in attachment to the tendon 130. The lubricious bearing surface 404 slides along knee anatomy during articulation. Through holes 400 are further provided and sized and shaped to receive fastening structure 410 for assuring a strong affixation to the tendon 130. In this way, relative movement between the implant 400 and ligament is eliminated and the implant 400 is thus always correctly positioned to provide desired tensioning and contact force load manipulation and absorption.

Figure 12:
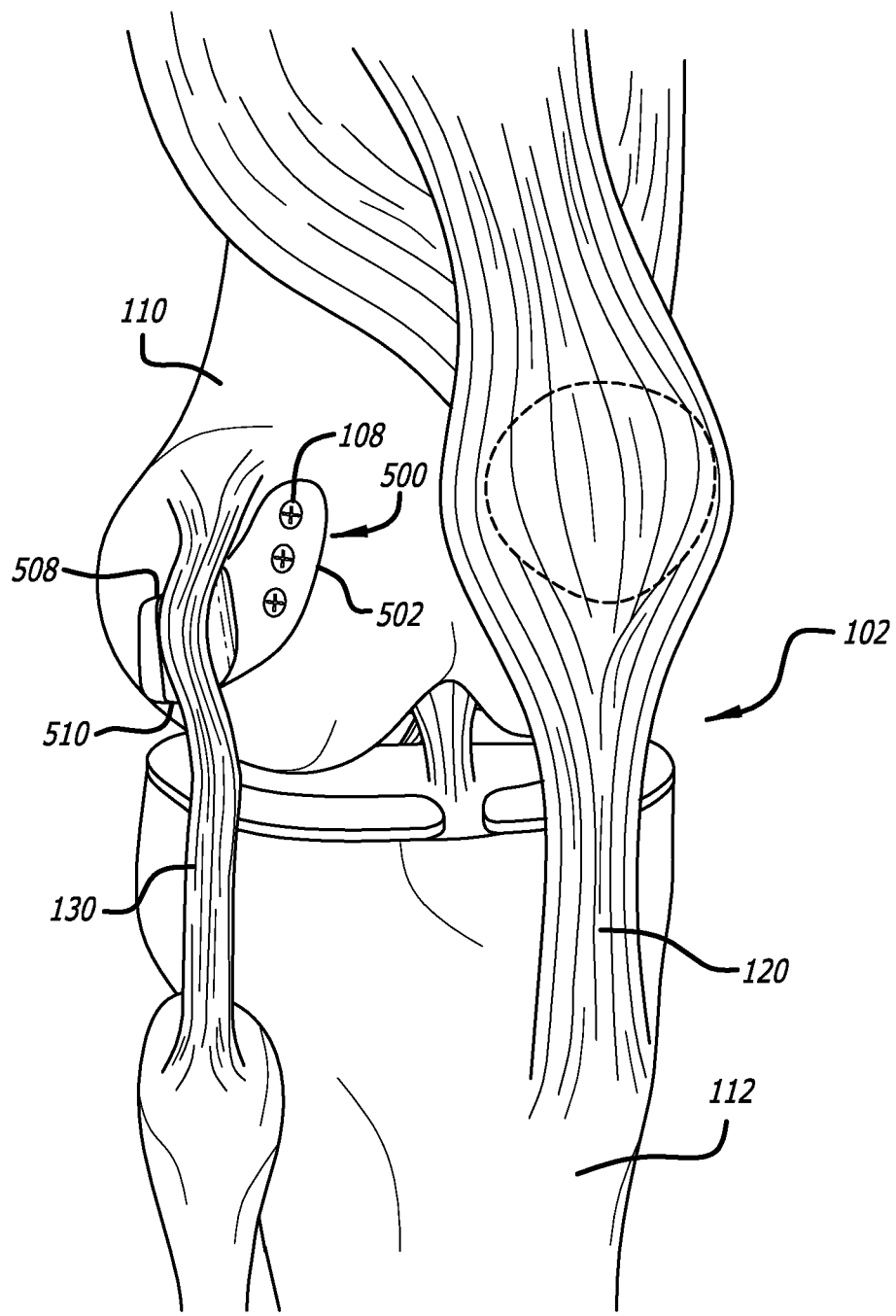
FIG. 12 is a side view, depicting yet another embodiment of an implant placed at a joint.

With reference to FIG. 12, there is shown in yet another embodiment of an implant 500. This implant 500 can include one or more of the above described features, such as one or more chambers, and further embodies a generally inverted J-shape. A vertically extending portion 502 of the implant 500 is provided with through holes sized and shaped to receive fastening structure such as bone screws 108. A laterally extending portion 508 includes a recess 510 for receiving a tendon 130. Although the implant 500 is shown attached to the tibia 112, it can also be affixed to the femur 110 or fibula 114 as well. This approach illustrates that an asymmetric implant can be employed to accomplish desired treatment of the knee joint. A further deviation would be to eliminate the vertically extending portion 502 and to include affixation structure within the recess 510. The J-shaped implant 500 can also function as a hook to change the path of the tendon.

The implants described herein are designed to displace a tendon or other anatomical, joint spanning structure in a direction away from the joint to increase the tension in the tendon or other structure. The increased tension causes load to be transferred within the joint structure. For, example an laterally placed implant increases the tension in the lateral ligaments and shifts a portion of the load in the knee joint from the medial surfaces to the lateral surfaces of the joint. Although the displacement of the tendon is shown as generally in a direction away from the joint, other displacement of the tendon can also function to increase tension and redistribute forces in the joint. In one example, a J-shaped or hook shaped implant can displace a portion of a ligament in an anterior or posterior direction causing the ligament to travel along a longer trajectory than the natural trajectory increasing tension in the ligament.

Conventional approaches to inserting the above-described implants within knee anatomy are contemplated. Arthroscopic approaches can be employed along with fluoroscopy or other imaging techniques to properly position the treatment devices. Prior to implantation, the anatomy of the patient's knee is assessed to determine a best course of treatment, and to identify a configuration of implant which best suits the patient's specific condition. The knee is rotated and turned through its full range of motion to identify proper implantation sites and to access the best manner for redistributing tensions and contact forces, with the objective of reducing pain. Further, the implant can be configured in its most compressed configuration for implantation and then reconfigured to function in a treatment capacity. Subsequent to implantation, the implant can be reconfigured to present an altered profile to achieve optimum results.

The foregoing therefore provides an implant embodying a compliant bolster and lengthening affect to increase a moment arm of the bolstered tendon for the purpose of relieving pain or other symptoms involving the knee. The size or stiffness of the implant can be altered to achieve the desired bolstering or manipulation of tension and contact forces. In general, for positioning an implant on the medial or lateral side of the knee joint having a height selected to increase tension in the tendon by at least 5 pounds can provide opening of the joint space on the opposite side of the knee joint an associated pain relief.

Figure 13:
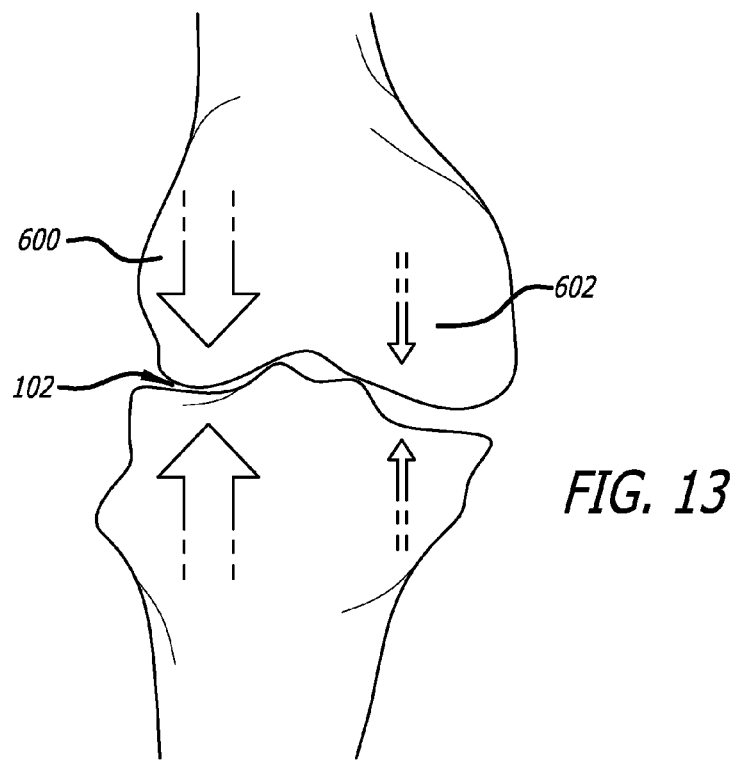
FIG. 13 is a cross-sectional view, depicting excessive overload of a lateral compartment of a knee joint.

As noted above, the anatomy of the lateral side of the knee joint is complicated as compared with the medial side. Thus, real estate for an implant is limited on the lateral side of the knee joint 102. However, osteoarthritis can of course affect either side of a knee joint. As shown in FIG. 13, there can exist for example, an excessive overload of a lateral compartment of a knee. Here, the larger arrows indicate greater forces in a joint on a lateral side 600 of a joint 102 as compared with the medial side 602. One treatment modality is to unload the lateral compartment by moving load onto the medial compartment using an implant attached to the medial knee. The implant is contemplated to actively import a varizing load to the knee and to unload the lateral compartment.

Figure 14:
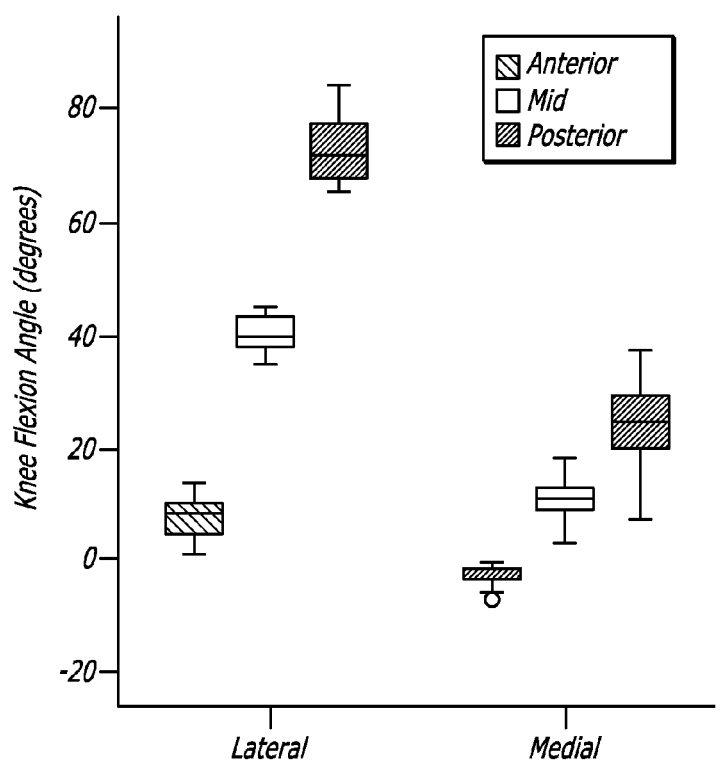
FIG. 14 is a graphical representation, depicting knee flexion angles for lateral and medial osteoarthritis patients.

To be an effective treatment, however, such imparting of varizing loads should take into consideration one or both of specific characteristics of lateral osteoarthritis and the kinematic patterns of the lateral side of a knee joint. With reference to FIG. 14, there is shown a relationship between knee flexion angles and the occurrence of contact between femoral lesion margin and midpoint contact with the tibia. Clearly, such contact occurs over a much larger range of angles of flexion for the lateral side of a knee joint (from zero to over eighty degrees of flexion) as compared with the medial side (from zero to less than forty degrees). Thus, a successful treatment modality for lateral OA should work over a large range of flexion angles and should operate to unload the joint in flexion as well as extension. Further, if OA can be identified to be mainly in the anterior, mid, or posterior portion of the lateral compartment, treatment can be tailored to unload at the appropriate flexion angle. For example, unloading at 1-10 degrees for anterior OA, unloading at 35-45 degrees for mid lateral compartment OA, and unloading at 60-80 degrees for posterior OA. For an implant designed to unload the entire lateral compartment, the implant is preferably designed to tension the medial ligaments and/or tendons over at least 50 degrees of motion and more preferably over at least 70 degrees of motion.

Figure 15:
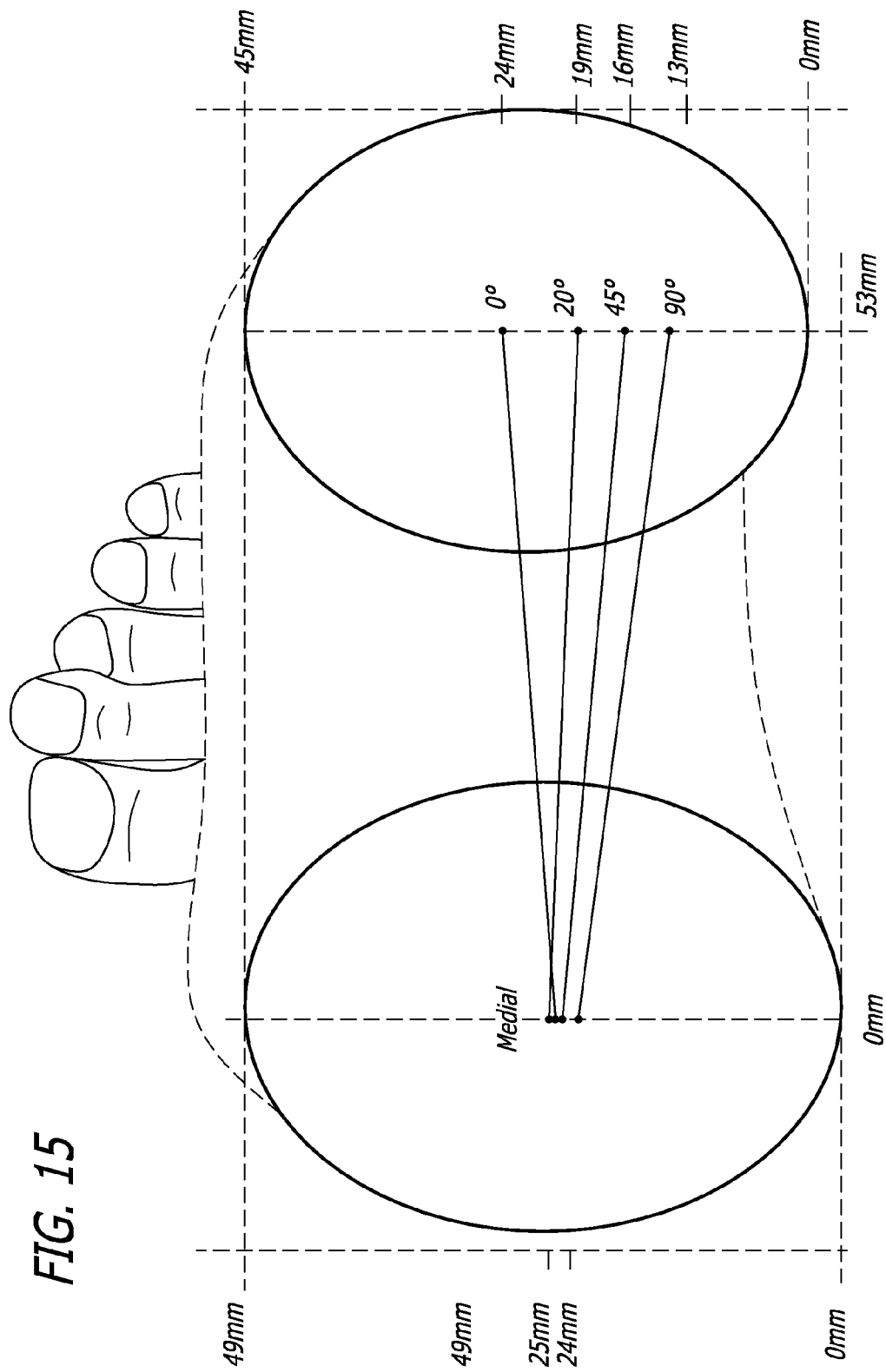
FIG. 15 is a graphical representation, depicting kinetic patterns of a knee joint.

Moreover, as shown in FIG. 15, the motions of the lateral knee are much broader than that of the medial knee. That is, the spacing within the medial capsule between the femur and tibia falls within a relatively narrow height, ranging around 24 mm to 25 mm, whereas the spacing within the tibial capsule decreases from 24 mm at 0° flexion to 13 mm at 90° flexion. With this broad kinematic pattern on the lateral side of a knee joint, the kinematic requirements for implants utilizing lateral attachment points necessarily increases. Accordingly, both the lack of real estate and the greater range of movement on the lateral side of the knee joint suggest implanting a device for treating lateral osteoarthritis on the medial side.

Figure 17A:
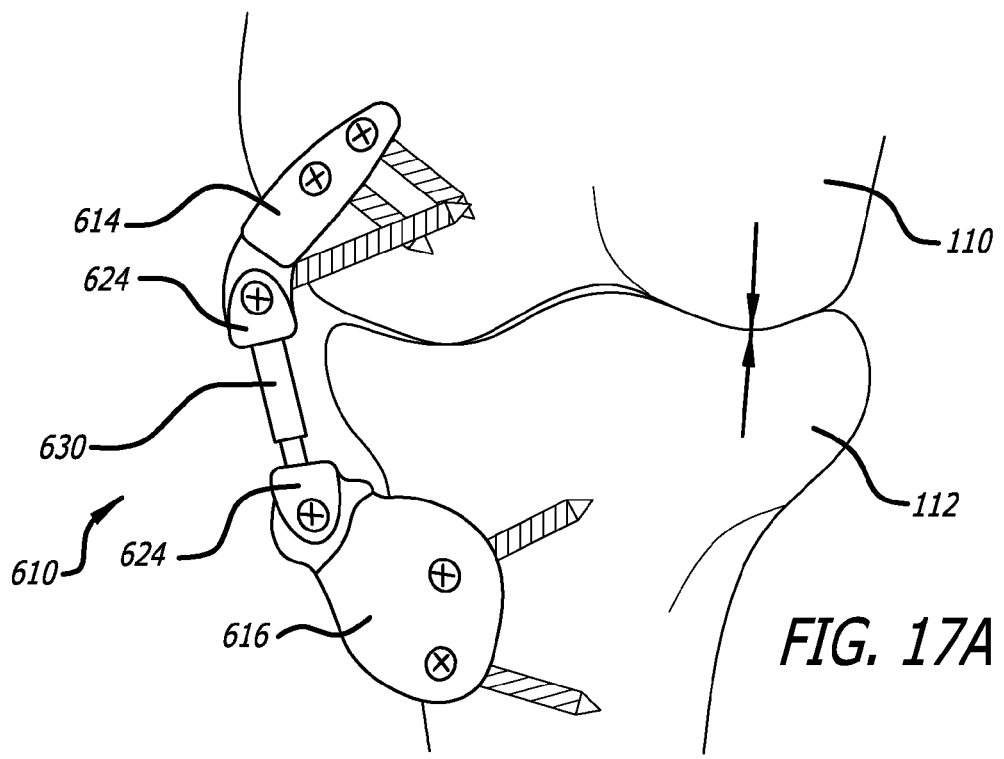
FIGS. 17A-B are cross sectional views, depicting the assembly of FIG. 16 attached across a joint.
Figure 17B:
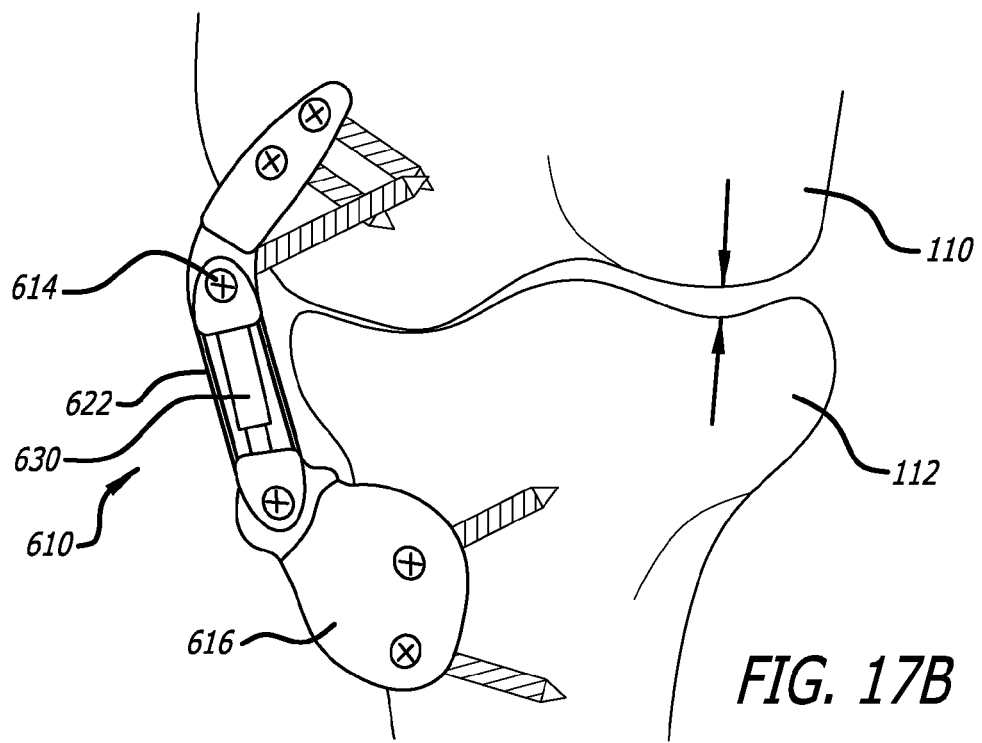

In one embodiment and treatment approach, an active unloading assembly 610 is contemplated to be configured across a knee joint (See FIGS. 16-17B). The active component of the assembly 610 is a tension assembly 612 configured to apply a varizing tension force to unload the lateral component. Thus, the tension assembly 612 and remaining portions of the active unloading assembly 610 are affixed to a medial side of a knee joint 102 to thereby create the desired tension force for unloading the lateral compartment. It is also contemplated that the devices can be attached on other joints and at various angles and various sides of joints to create other desired effects.

The active unloading assembly 610 can further include a first base assembly 614 for attachment to a femur 110, as well as a second base assembly 616 for attachment to a tibia 112 (FIGS. 17A-B). Extending from each base 614, 616 can be a projection 620 configured to receive opposite ends of the tensioning assembly 612. The projections 620 are configured to provide an articulating connection between the bases 614, 616 and the tensioning assembly 612.

The tension assembly 612 includes a tension loop 622 configured about a pair of spaced collars 624. The collars 624 are each sized and shaped to receive one base projection 620 and to provide an articulating structure. Although the collars 624 as shown connected to the bases in an articulating manner by projections, other methods of connecting the collars to the bases in an articulating manner may also be employed, such as ball and socket joints. Alternatively, the collars may be formed integrally with the bases and the articulation may be omitted in which case the flexibility required by the system would be provided by the tension loop alone. The articulating structure accommodates the motion of the members of a joint 102 during flexion and extension. Further, a telescoping piston assembly 630 can be configured between the collars 624, the same helping to ensure the integrity and stability of the system. As the joint members transition between flexion and extension, the member of the piston assembly 630 slide with respect to each other. In some situations where the added stability is not needed, the telescoping assembly can be omitted.

The tension loop 622 as shown in the present application is a biocompatible elastomeric band having a circular cross section. However, other types of tension bands, cables or springs may also be used.

Employing conventional techniques, the active loading assembly is implanted on a medial side, and across a knee joint. The tension assembly 612 operates to apply a varizing force to the lateral compartment during the natural motion of the knee, so as to off-load the lateral compartment to address an osteoarthritic condition. It is further contemplated that the tension can be applied during less than a full cycle of limb articulation or throughout an entire flexion-extension cycle. It is also contemplated that a contact or variable tension force is provided by the assembly.

Figure 18:
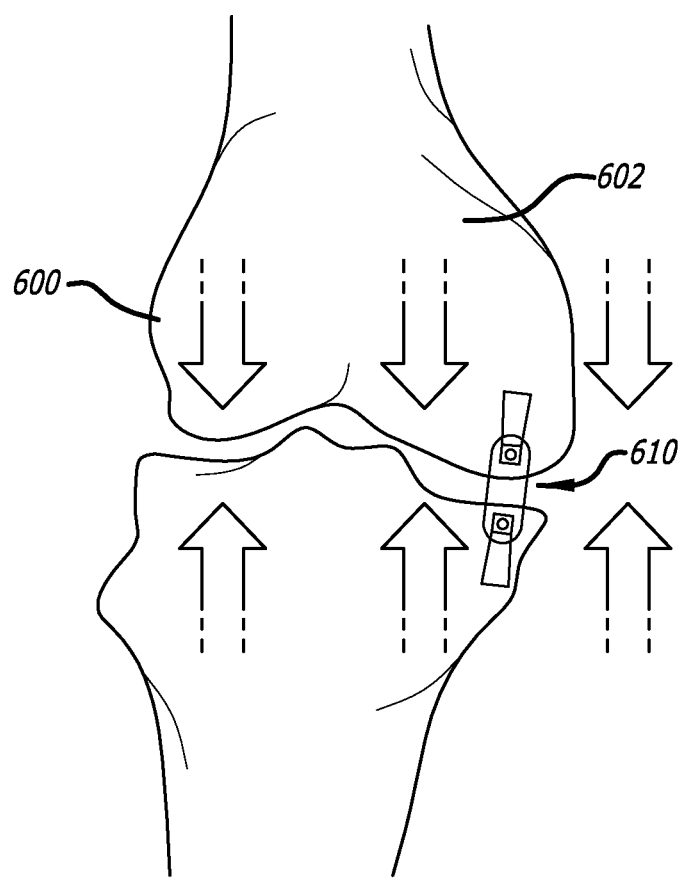
FIG. 18 is a cross-sectional view, depicting forces on a joint treated with the active unloading assembly.

With reference now to FIG. 18, there is shown the forces on a joint after treatment with the active unloading assembly. As shown, the forces on the lateral side 600 of a knee joint, as compared with those previously existing in an untreated joint shown in FIG. 13 are decreased, and forces are generally balanced across the joint. Pain associated with undisclosed forces associated with lateral osteoarthritis is thus remedied.

Thus, it will be apparent from the foregoing that, while particular forms of the invention have been illustrated and described, various modifications can be made without parting from the spirit and scope of the invention. In particular, one or more features of one specific approach can be incorporated into another approach. Additionally, the present disclosure can be made to be applicable to other medical conditions.

We claim:

1. A method of treating lateral osteoarthritis of a joint, comprising:

implanting a treatment assembly on a medial side of a knee joint, wherein the treatment assembly includes an active unloading assembly including a first base, a second base, a tension member configured between the first and second bases, the treatment assembly includes a first collar associated with the first base and a second collar associated with the second base and wherein the tension member is configured about the first and second collars, and the treatment assembly further includes a piston attached at its ends to the first and second collars; and imparting a varizing load to the joint to unload a lateral knee compartment.

2. The method of claim 1, further comprising applying a tension across bones defining the joint on the medial side to unload the lateral knee compartment.

3. The method of claim 1, further comprising attaching the first base to a first bone of the joint and attaching the second base to the second bone of the joint.

4. The method of claim 3, further comprising configuring the tensioning member to impart a tension between the first and second bones.

5. The method of claim 1, wherein the treatment assembly applies tension throughout a complete flexion-extension cycle of the joint.

6. The method of claim 1, wherein the treatment assembly applies tension throughout less than a complete flexion-extension cycle of the joint.

7. The method of claim 1, wherein tensioning member includes a elastomeric member.

* * * * *